(12) United States Patent
Menz

(10) Patent No.: US 6,211,248 B1
(45) Date of Patent: Apr. 3, 2001

(54) FLUORINATED ALKANES AND THEIR USES

(75) Inventor: Dirk-Henning Menz, Diedorf (DE)

(73) Assignee: Pharm Pur GmbH, Augsburg (DE)

( * ) Notice: Subject to any disclaimer, the term of this patent is extended or adjusted under 35 U.S.C. 154(b) by 0 days.

(21) Appl. No.: 09/074,252

(22) Filed: May 7, 1998

(30) Foreign Application Priority Data

May 7, 1997 (DE) ............................................. 197 19 280

(51) Int. Cl.⁷ .................................................... A61K 31/02
(52) U.S. Cl. .............................................................. 514/743
(58) Field of Search .................................. 424/350, 351; 260/653, 653.3; 514/743

(56) References Cited

U.S. PATENT DOCUMENTS 4,173,654  11/1979  Scherer.
5,275,669  1/1994  Van Der Puy et al..

FOREIGN PATENT DOCUMENTS

| 195 36 504 A1 | 9/1995 | (DE). |
| 0 381 986 A1 | 1/1990 | (EP). |
| 0 444 752 A1 | 2/1991 | (EP). |
| 0 563 446 A1 | 11/1992 | (EP). |
| 91/01759 A1 | 7/1990 | (WO). |
| 96/40052 A1 | 6/1996 | (WO). |

*Primary Examiner*—Elli Peselev
(74) *Attorney, Agent, or Firm*—Larson & Taylor PLC

(57) ABSTRACT

The invention concerns a partially fluorinated alkane with the general formula $R_F[CF_2—CH_2]R_H$, wherein $R_H$ is a substituent of the general formula $C_nH_x$ selected from the group consisting of n-alkyl, sec-alkyl, tert-alkyl and cycloalkyl; $R_F$ is a substituent of the general formula $C_mF_x$ selected from the group consisting of the perfluoro-n-alkyl, perfluoro-sec-alkyl, perfluoro-tert-alkyl, and perfluorocycloalkyls, with the proviso that only one of $R_F$ and $R_H$ can be linear, and that $n>3$, the sum of $n+m<18$ and that only either $R_H$ or $R_F$ are an n-alkyl or perfluorinated n-alkyl. These partially fluorinated alkanes find use as solvents, especially in medical applications where the properties of hydrocarbon solvents are not acceptable, in implants, and as an oxygen carrying blood substitute.

5 Claims, No Drawings

FLUORINATED ALKANES AND THEIR USES

The invention concerns partially fluorinated alkanes according to the general formula I:

$$R_F[CF_2-CH_2]R_H \quad \text{I}$$

wherein $R_H$ is a substituent of the general formula $C_nH_x$, and $R_F$ is a substituent of the general formula $C_mF_x$.

In the event that sec-alkyls, tert-alkyls or cycloalkyls, or the perfluoro equivalents variants of these alkyl groups are used, the molecule is branched. Linear or branched molecules of this type are described, for example, in DE 42 05 341 A1 and in U.S. Pat. No. 5,275,669. Furthermore, the use of such alkanes in medicine, pharmacy and technology is known from these and other publications. Especially in DE 42 05 341 A1, the reduction of the concentration plays a decisive role which is reflected in the selection of compositions with short perfluorinated substituents. DE 195 36 504 A1 also describes fluorinated alkanes and their use.

Moreover, it is known that by extending the $R_F$ or $R_H$ substituents, and by combining various long substituents in such compositions, the surface and interfacial properties at phase boundaries to other media or surfaces treated with such compositions may be influenced. Associated therewith is the formation of hydrophilic or hydrophobic properties, which are reflected in dissolving properties or dissolving intermediary properties and in surface-active properties.

The variations of the $R_F$ or $R_H$ substituents known from the prior art, however, do not generally produce any alkanes with optimum biocompatible properties, since the aggregated systems produced by the interaction with other substances are often unstable. In this way, undesirable separations and short life spans of the mixtures and emulsions result.

In this context, biocompatibility refers both to the chemical inertness of a substance and its tissue tolerance.

The aforementioned problems of the known substances also occur in applications in which the biocompatibility is not of significance. Undesirable separation processes and short life spans of the substances are disadvantageous in every application, in particular, when using these substances as medical or technical solvents.

Thus, it is the object of this invention to further improve such a partially fluorinated alkane in such a way that the developing aggregated systems are more stable.

This invention in its broadest embodiment comprises partially fluorinated alkanes according to the general formula I:

$$R_F[CF_2-CH_2]R_H \quad \text{I}$$

wherein $R_H$ is a substituent of the general formula $C_nH_x$ selected from the group consisting of n-alkyl, sec-alkyl, tert-alkyl or cycloalkyl; $R_F$ is a substituent of the general formula $C_mF_x$ selected from the group consisting of n-perfluoralkyl, s-perflouroalkyl, t-perfluoroalkyl or perfluorocycloalkyl; $n \geq 3$; and the sum of $n+m<18$; with the provisos that:

(i) if $R_H$ is n-alkyl, $R_F$ is other than n-perfluoroalkyl, and (ii) if $R_F$ is n-perfluoroalkyl, $R_H$ is other than n-alkyl.

Preferably, $n>7$ and m is between 5 and 8. More preferably, $m>5$ and n is between $m-1$ and $m+2$.

Preferably, the ratio of the steric volume of $R_F$ to $R_H$ is less than 0.7. Alternatively, the ratio of the steric volume of $R_F$ to $R_H$ is greater than 1.3.

It can thus be seen that in the compounds of this invention the desired properties are obtained when the alkane substituent $R_H$ contains at least four carbon atoms, the sum of the carbon atoms in the hydrogen substituent $R_H$ and in the fluorine substituent $R_F$ is less than 18 and also at least one of the two substituents (hydrogen substituent $R_H$ or perfluoro substituent $R_F$) is formed like a branched alkyl.

For example, the fluorine substituent $R_F$ can be an n-perfluoroalkyl group, and the hydrogen substituent $R_H$ can be a sec-alkyl, tert-alkyl or a cycloalkyl group. Alternatively, the hydrogen substituent $R_H$ can be an n-alkyl group, and the fluorinated substituent is then branched, i.e. is a sec-perfluoroalkyl, a tert-perfluoroalkyl, or a perfluorocycloalkyl group. Both substituents $R_F$ and $R_H$ can also be branched; however, according to the invention, it is excluded that both substituents $R_H$ and $R_F$ are linear.

The compounds of this invention are synthesized by using conventional methods.

The described compositions are, in particular, highly purified prior to medical applications, by using known conventional processes. The compositions thus produced are then completely non-toxic since substitute reactions cannot occur either on the spacer group $CF_2-CH_2$ or on the perfluorinated portion of the composition which would lead to toxic effects. The special solvent properties of the compositions are based the fact that they not only combine the properties of pure perfluorocarbons with the properties of pure hydrocarbons but form, after the dissolving process, aggregated systems of various structures which are stabilized by the anisotropic structure of the compositions according to the invention. This is made possible by the selection of the substituents according to the invention, whereby the different spatial requirements of the $R_F$ and $R_H$ substituents are also significant. The structural stabilization of the aggregated systems suppresses the separation of the resultant solutions and increases the solvent power of the compositions. Comparable effects can only be attained in purely linear $R_F-R_H$ compositions by substantially longer chain lengths, or by differences in chain lengths which simultaneously results in undesirable properties such as, for example, higher boiling points or wax-like compositions as a result of which it can generally no longer be used as a biocompatible solvent and liquid implant, and the other applications are also only possible to a limited degree.

The alkane according to the invention can be advantageously used especially in the following cases of application.

Due to the dissolving power for hydrocarbons, in particular, mineral oils, tar and silicone oils, the partially perfluorinated alkanes according to the invention enable the purification of tissues contaminated with such substances. The contaminations form stable solutions with the alkanes of the invention, so that they can be washed out. In this way, silicone oils which escaped from defective implant cushions or used as liquid implants in ophthalmology, are carefully removed. The partially fluorinated alkanes according to the invention are especially suitable for attending to injuries into which oils, tar or fats based on mineral oil have penetrated. In particular, the removal of combustion residues from burn injuries is also possible. As a result of the ability of the partially perfluorinated alkanes of the invention to transport oxygen, the decontamination of tissues is additionally promoted by supplying them with oxygen.

An essential difference between partially fluorinated alkanes of the invention and conventional solvents is due to the fact that conventional solvents persistently damage tissue to be treated, but the partially fluorinated alkanes of the invention do not.

Furthermore, the partially fluorinated alkanes of the invention can be used to assist in the regeneration of tissue in smoker's lungs in that deposits within the lung are washed out by rinsing the lung. Due to the high dissolving power of the partially fluorinated alkanes according to the invention for oxygen and carbon dioxide, the oxygen supply can be maintained and the removal of carbon dioxide is not interrupted.

In their function as solvents, the partially fluorinated alkanes of the invention have the advantage that the size and spatial structure of the $R_F$ and $R_H$ substituents may be selected so as to be able to extract contaminants with minimum tissue penetration.

The biocompatible properties and the low surface tension as well as the special interfacial properties of the partially fluorinated alkanes make it possible to use these compositions as liquid implants. An example thereof is the use in ophthalmology, e.g. as a vitreous body substitute, as retina developing agents, as an aid in the laser coagulation of the retina or as post-operative retina tamponage.

If undesirable substances, e.g. silicone oil, tar or fats are to be washed out in the field of ophthalmology or for the care of wounds, very active solvents must often be used which can, however, persistently damage the tissue. The partially fluorinated alkanes according to the invention can be advantageously used in a two-step process. In a first step, the silicone oil, the tar or the fat can be rinsed out with an effective but perhaps tissue-damaging solvent. In a second subsequent step, this solvent is washed out with one of the partially fluorinated alkanes of the invention.

The process described can also be carried out in several steps, whereby individual effects of these solvents can be used in a time-limited manner by means of a step-by-step exchange of solvents, and can thus be optimally adapted to the therapeutic requirements. In these processes, some or all of the solvents applied can be partially fluorinated compounds according to the invention.

Similarly, the partially fluorinated alkanes of the invention can be used as a liquid scalpel with aid of a highly effective solvent. For this purpose, a solvent is first introduced which intentionally attacks tissue components and which is subsequently "deactivated" by adding one of the alkanes of the invention. This corresponds to a chemical alternative to the actions of enzymes known in the biological field which are already used for such specific breakdown reactions.

Due to the amphiphilic character of the compositions, further fields of applications are made accessible. The partially fluorinated alkanes according to the invention can form micro-emulsions with pharmacological substances in which the active substances are included by the partially fluorinated alkanes. In this way, so-called "slow drug release" systems can be built up, i.e. substances which include one or more specific pharmacological products and only release these slowly.

A further use of the amphiphilic character of the partially fluorinated alkanes according to the invention is the stabilization of oxygen-transporting media which are built up from emulsions of perfluorinated compositions. Oxygen-transporting media are of importance especially as blood substitutes or in liquid artificial respiration.

The alkanes of the invention can, in addition, also be used in technology due to their special dissolving properties, namely as cleansers and/or solvents. This is especially advantageous when a direct contact of the person with the solvent cannot be avoided or residues of solvents remain on or in the technical or medicotechnical products treated with these solvents and cannot be completely removed and thus reach the human body. This includes the cleaning of implants and prostheses as well as the application of thin silicone oil films on tubules and other medico-technical devices to improve their ability to slide.

Furthermore, the partially fluorinated alkanes of the invention can themselves be used as lubricants wherein, for example, plastic surfaces are rubbed with these compositions. The partially fluorinated alkanes thereby align themselves in such a way that the $R_H$ substituent is directed to the plastic surface and the $R_F$ group containing fluorinated groups is directed outward which modify the surface properties in a known manner.

When used as solvent for hydrocarbons and silicone oils, the partially fluorinated alkanes of formula I have proven to be especially advantageous, in which n>7 and m has a value of between 5 and 8. When used as a liquid implant, and as an implant with tamponing action, the partially fluorinated alkanes of formula I are especially advantageous when m>5 and n has a value of between m−1 and m+2.

In the use as amphiphile, the partially fluorinated alkanes of formula I are especially advantageous when the ratio of the steric volume of the substituents $R_F$ to $R_H$ is less than 0.7 or greater than 1.3.

As noted above, the synthesis of the alkanes according to the invention follows conventional procedures for the synthesis of compounds of this general type. For example, the partially fluorinated alkane of formula II

$$CF_3CF_2CF_2CF_2\text{---}CF_2CH_2\text{---}CH(CH_3)_2 \qquad \text{II}$$

which has a boiling point of 143° C., can be produced by dehydration of isopropanol, followed by the addition of perfluoro-1-iodopentane, and reaction with a Zn/HCl mixture. The required partially fluorinated alkane is separated by distillation, followed by conventional purification.

EXAMPLES

Example 1

Preparation of 1-Perfluorobutyl-2-Methyl-Propane, $CF_3(CF_2)_3CH_2CH(CH_3)_2$.

Perfluoro-1-iodobutane is purged for 30 min. with nitrogen together with AIBN (azo-bis-isobutyronitrile) as radical starter in an autoclave while cooling. Isobutene is subsequently condensed into the autoclave in the molar ratio. The autoclave is then sealed and heated to 90° C. while being stirred and stirred further for about 6 h at this temperature. After the separation by distillation of an unreacted starting substance (vigreux column, reduced pressure), it is dehalogenated in a hydrogenating manner with Zn/HCl and the product fractionated in the vacuum via a vigreux column. Boiling point.: 70°/60 Torr. The product is then highly purified according to a known process.

Example 2

Preparation of 1-Perfluorohexyl-2-Methyl-Propane, $(CF_3(CF_2)_5CH_2CH(CH_3)_2$.

Perfluoro-1-iodohexane is purged for 30 min with nitrogen together with AIBN as radical starter in autoclave while cooling and isobutene is subsequently condensed into the autoclave in the molar ratio. After sealing, the autoclave is heated to 90° C. while being stirred and stirred further for about 6 h at this temperature. After the separation by distillation of an unreacted starting substance (vigreux column, reduced pressure), the product is dehalogenated in a hydrogenating manner with Zn/HCl and the product fractionated in the vacuum via a vigreux column. Boiling point.: 80°/60 Torr. The product is then highly purified according to a known process.

Example 3
Preparation of 1-Perfluorobutyl-3-Methyl-Butane, $CF_3(CF_2)_3(CH_2)_2CH(CH_3)_2$.

Isoamyl alcohol is transformed into the corresponding pentene with 85% phosphoric acid, purified by distillation and placed in an autoclave in a molar ratio with perfluoro-1-iodobutane. After adding AIBN, it is purged for 30 min with $N_2$ while cooling and the procedure set out in Example 1 followed. Boiling point.: 65°/60 Torr.

Example 4
Preparation of 1-Perfluorohexyl-3-Methyl-Butane, $CF_3(CF_2)_5CH_2CH(CH_3)CH_2CH_3$.

Isoamyl alcohol (isomers) is transformed into the corresponding pentene with concentrated sulphuric acid, purified by distillation and placed in an autoclave in a molar ratio with perfluoro-1-iodohexane. After adding AIBN, it is purged for 30 min with $N_2$ while cooling and the procedure set out in Example 1 followed. Boiling point.: 85°/60 Torr.

What is claimed is:

1. A biocompatible solvent for perfluorocarbons and hydrocarbons comprising a partially fluorinated alkane according to the formula I:

$$R_F[CF_2-CH_2)R_H$$

wherein:
$R_H$ is a substituent of the formula $C_nH_x$ selected from the group consisting of n-alkyl, sec-alkyl, tert-alkyl and cycloalkyl;
$R_F$ is a substituent of the formula $C_mF_x$ selected from the group consisting of, n-perfluoroalkyl, sec-perfluoroalkyl, tert-perfluoroalkyl and perfluorocycloalkyl; $n \geq 3$; and the sum of n+m<18;
with the provisos that:
(i) if $R_H$ is n-alkyl, $R_F$ is other than n-perfluoroalkyl, and
(ii) if $R_F$ is n-perfluoroalkyl, $R_H$ is other than n-alkyl.

2. A composition comprising oxygen-transporting medium and a stabilizing amount of a partially fluorinated alkane according to the formula I: $R_F[CF_2-CH_2]R_H$
wherein:
$R_H$ is a substitutent of the formula $C_nH_x$, selected from the group consisting of n-alkyl, sec-alkyl, tert-alkyl and cycloalkyl;
$R_F$ is a substituent of the formula $C_mF_x$, selected from the group consisting of n-perfluoroalkyl, sec-perfluoroalkyl, tert-perfluoroalkyl and perfluorocycloalkyl; $n \geq 3$; and the sum of n+m<18;
with the provisos that:
(i) if $R_H$ is n-alkyl, $R_F$ is other than n-perfluoroalkyl, and
(ii) if $R_F$ is n-perfluoroalkyl, $R_H$ is other than n-alkyl.

3. A vitreous body substitute or retina developing agent or aid in laser coagulation on the retina or solvent for medications or post-operative retina tamponage including a partially fluorinated alkane according to the formula I:

$$R_F[CF_2-CH_2)R_H$$

wherein:
$R_H$ is a substituent of the formula $C_nH_x$, selected from the group consisting of n-alkyl, sec-alkyl, tert-alkyl and cycloalkyl;
$R_F$ is a substituent of the formula $C_mF_x$ selected from the group consisting of n-perfluoroalkyl, sec-perfluoroalkyl, tert-perfluoroalkyl and perfluorocycloalkyl; $n \geq 3$; and the sum of n+m<18;
with the provisos that:
(i) if $R_H$ is n-alkyl, $R_F$ is other than n-perfluoroalkyl, and
(ii) if $R_F$ is n-perfluoroalkyl, $R_H$ is other than n-alkyl.

4. A method of regenerating lung tissue by rinsing the lung tissues with a partially fluorinated alkane according to the formula I:

$$R_F[CF_2-CH_2]R_H$$

wherein:
$R_H$ is a substituent of the formula $C_nH_x$, selected from the group consisting of n-alkyl, sec-alkyl, tert-alkyl and cycloalkyl;
$R_F$ is a substituent of the formula $C_mF_x$ selected from the group consisting of n-perfluoroalkyl, sec-perfluoroalkyl, tert-perfluoroalkyl and perfluorocycloalkyl; $n \geq 3$; and the sum of n+m<18;
with the provisos that:
(i) if $R_H$ is n-alkyl, $R_F$ is other than n-perfluoroalkyl, and
(ii) if $R_F$ is n-perfluoroalkyl, $R_H$ is other than n-alkyl.

5. A method of treating and cleaning wounds comprising burn wounds by applying to the affected area a partially fluorinated alkane according to the formula I:

$$R_F[CF_2-CH_2]R_H$$

wherein:
$R_H$ is a substituent of the formula $C_nH_x$ selected from the group consisting of n-alkyl, sec-alkyl, tert-alkyl and cycloalkyl;
$R_F$ is a substituent of the formula $C_mF_x$ selected from the group consisting of n-perfluoroalkyl, sec-perfluoroalkyl, tert-perfluoroalkyl or perfluorocycloalkyl; $n \geq 3$; and the sum of n+m<18;
with the provisos that:
(i) if $R_H$ is n-alkyl, $R_F$ is other than n-perfluoroalkyl, and
(ii) if $R_F$ is n-perfluoroalkyl, $R_H$ is other than n-alkyl.

* * * * *